(12) United States Patent
Zakutin

(10) Patent No.: US 8,015,987 B2
(45) Date of Patent: Sep. 13, 2011

(54) VIBRATION-TYPE CLEANING DEVICE FOR CONTACT LENSES

(76) Inventor: David Michael Zakutin, Breslau (CA)

( * ) Notice: Subject to any disclaimer, the term of this patent is extended or adjusted under 35 U.S.C. 154(b) by 278 days.

(21) Appl. No.: 12/003,856

(22) Filed: Jan. 2, 2008

(65) Prior Publication Data

US 2009/0283118 A1 Nov. 19, 2009

(51) Int. Cl.
*B08B 3/04* (2006.01)
*B08B 3/12* (2006.01)
*A45C 11/00* (2006.01)

(52) U.S. Cl. .......... 134/184; 134/117; 134/901; 206/5.1

(58) Field of Classification Search .................. 134/901, 134/117, 184; 206/5.1
See application file for complete search history.

(56) References Cited

U.S. PATENT DOCUMENTS

| | | | | |
|---|---|---|---|---|
| 3,851,861 A | * | 12/1974 | Cummins et al. | 366/114 |
| 4,582,076 A | * | 4/1986 | Prat | 134/57 R |
| 4,691,725 A | * | 9/1987 | Parisi | 134/184 |
| 4,957,128 A | * | 9/1990 | Chen | 134/118 |
| 2007/0023064 A1 | * | 2/2007 | Gilbert et al. | 134/1 |
| 2008/0129166 A1 | * | 6/2008 | Benneche et al. | 312/292 |

FOREIGN PATENT DOCUMENTS

| | | | |
|---|---|---|---|
| JP | 09-054289 | * | 2/1997 |
| WO | WO 02/097518 | * | 12/2002 |
| WO | WO 03/038507 | * | 5/2003 |

* cited by examiner

*Primary Examiner* — Michael Kornakov
*Assistant Examiner* — Nicole Blan
(74) *Attorney, Agent, or Firm* — Muncy, Geissler, Olds & Lowe, PLLC

(57) ABSTRACT

A vibration-type cleaning device for contact lenses comprises an adaptor that is provided with a support part thereon for supporting a contact lens case and a base that is provided under the bottom of the adaptor. The base is connected with the adapter via a positioning element so that the base can be attached to or detached from the adaptor. The base is provided with a vibrator therein and the vibrator is connected with a power source. Consequently, the vibrator can be driven under the control of a user to vibrate the contact lens solution and the contact lenses in the contact lens case and the cleaning effect of the contact lenses in the contact lens solution can be enhanced through vibration.

23 Claims, 4 Drawing Sheets

VIBRATION-TYPE CLEANING DEVICE FOR CONTACT LENSES

BACKGROUND OF THE INVENTION

1. Field of the Invention

The present invention relates to a vibration-type cleaning device for contact lenses and, more particularly, to a vibration-type cleaning device for contact lenses comprising a base and an adaptor that can be attached to or detached from the base and is suitable for connection with contact lens cases of different specifications, where a vibrator is provided in the base for enhancing the cleaning effect of the contact lenses in the contact lens case and users can be reminded of the time when they have to dispose their contact lenses.

2. Description of the Prior Art

People with myopic problems usually wear glasses with frames in order to obtain normal or enough eyesight to maintain their normal vision performances. Recently, the glasses with frames are widely replaced by contact lenses under beauty consideration. However, corneas of users may suffer from anoxia that will cause injury to the corneas when people continuously wear contact lenses for a long period of time. Thereby, after wearing contact lenses for a certain period of time, people have to take off, wash, and clean their contact lenses for the next use.

Prior to soaking the contact lenses, manufacturers usually advise users to rub their contact lenses by their fingers in order to loosen foreign debris. The most common way to clean contact lenses is to put a pair of contact lenses into two containers of a contact lens case that is filled with clean solution and rub the contact lenses with fingers. Thereby, the dust, deposited proteins, mucus, oil stain, or other dirty things can be removed therefrom and the oxygen permeability of the contact lenses can be maintained. However, the cleaning way mentioned above may fail to work effectively if the fingers used to rub the contact lenses are unclean. Besides, the cleaning process is also time-consuming. Thereby, vibration is introduced as an alternative to the use of finger rubbing.

Different types of cleaning devices for contact lenses are invented recently and the contact lenses put in these cleaning devices can be shaken by hands, vibrated by motors, or shaken by ultrasonic agitation. When people clean their contact lenses by soaking their contact lenses in cleaning devices that is shaken by their hands, the contact lenses may be damaged if they exert too great a force to shake the cleaning devices. When people clean their contact lenses by using cleaning devices that is vibrated by motors or shaken by ultrasonic agitation, they are to put their contact lenses or contact lens cases into the cleaning devices to proceed with cleaning process. However, the specifications of contact lens cases that are manufactured by different companies are different. When people are in different countries or regions, they may use contact lens cases that are manufactured by different companies and thus are of different specifications. Thereby, people have to buy different cleaning devices according to the contact lens cases they use and it will be uneconomic for them to buy a variety of cleaning devices. Besides, these cleaning devices are not convenient to carry because of their relatively large size.

In order to solve the problems mentioned above to provide a cleaning device for contact lenses that is suitable for different specifications of contact lens cases and for economic purpose, is convenient to carry, and has effective cleaning function, inventor had the motive to study and develop the present invention after hard research.

SUMMARY OF THE INVENTION

The main object of the present invention is to provide a vibration-type cleaning device for contact lenses having a base, on which is provided with an adaptor that can be attached to or detached from the base. Thereby, adaptors of different specifications can be provided for connection with contact lens cases of different specifications and the cost for buying different cleaning devices can be saved.

Another object of the present invention is to provide a vibration-type cleaning device for contact lenses having a soundproof base, so that the noise can be reduced and the movement of the cleaning device can be restricted while limited freedom of movement is still allowed to enhance vibration transmission when the contact lenses are vibrated in the contact lens cases.

Another object of the present invention is to provide a vibration-type cleaning device for contact lenses having a control button and a display for inputting and showing the vibration time and the time when users have to dispose their contact lenses, so that users can be reminded timely in order to clean their contact lenses effectively and extend the lifetime of the contact lenses.

Another object of the present invention is to provide a vibration-type cleaning device for contact lenses having a positioning element that is magnetic and used for connecting the base and the adaptor, so that the base, the adaptor, and the contact lens case can be assembled easily and the size of the cleaning device can be reduced to carry conveniently.

In order to achieve the above objects, the present invention provides a vibration-type cleaning device for contact lenses comprising an adaptor and a base. The adaptor is disposed with a support part thereon for supporting a contact lens case. The base is connected with the adapter via a positioning element and is disposed with a vibrator therein. The vibrator is connected with a power source for driving the vibrator to vibrate the contact lens solution and the contact lenses in the contact lens case and the cleaning effect of the contact lenses in the contact lens solution is enhanced through vibration.

In practice, the base includes a bottom plate and a cover, wherein the cover covers the bottom plate and the bottom plate is provided with a groove for placing the vibrator.

In practice, the base is made of elastic plastics.

In practice, the present invention further includes a display, a microprocessor, and at least a control button and the display, the microprocessor, and the control button are in electric connection with the power source and the vibrator.

In practice, the positioning element includes a first magnetic piece and a second magnetic piece that are attractable with each other. The first magnetic piece is located in the base while the second magnet piece is located on the support part.

The following detailed description, given by way of examples and not intended to limit the invention solely to the embodiments described herein, will best be understood in conjunction with the accompanying drawings.

DETAILED DESCRIPTION OF THE PREFERRED EMBODIMENTS

Figure 1:
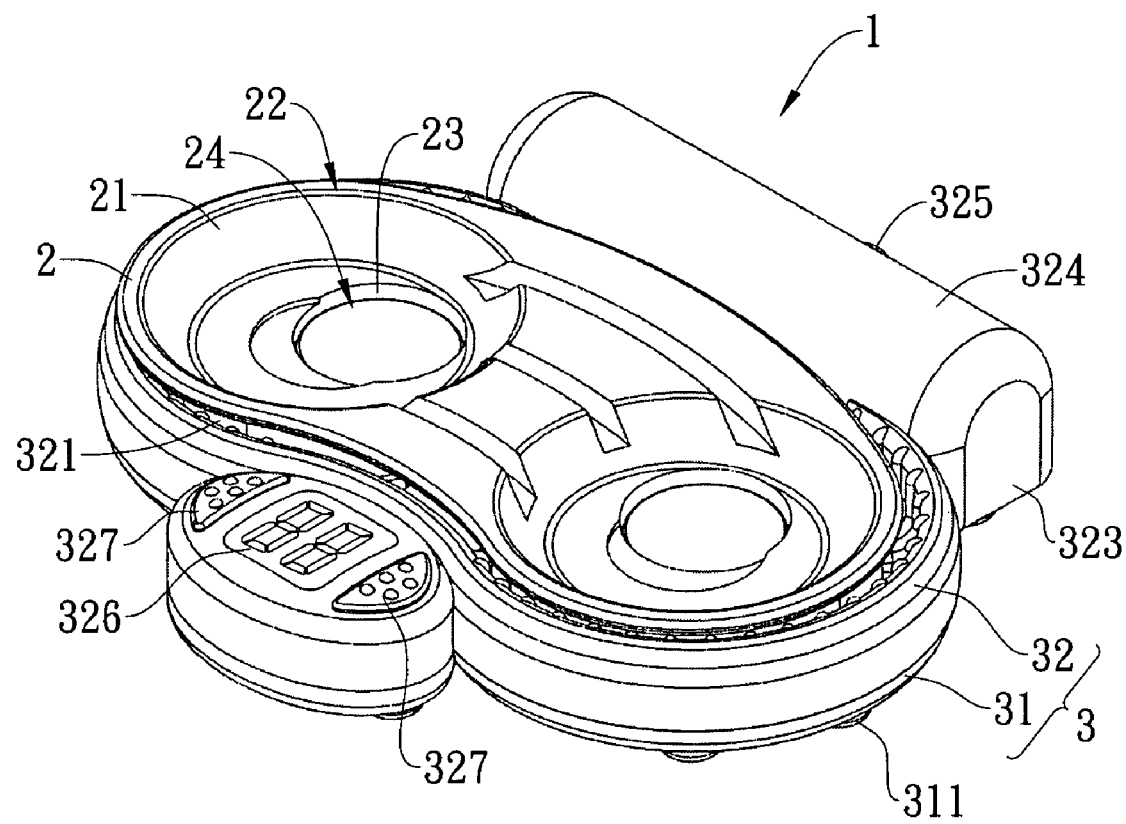
FIG. 1 is a perspective view of an embodiment of the present invention.
Figure 2:
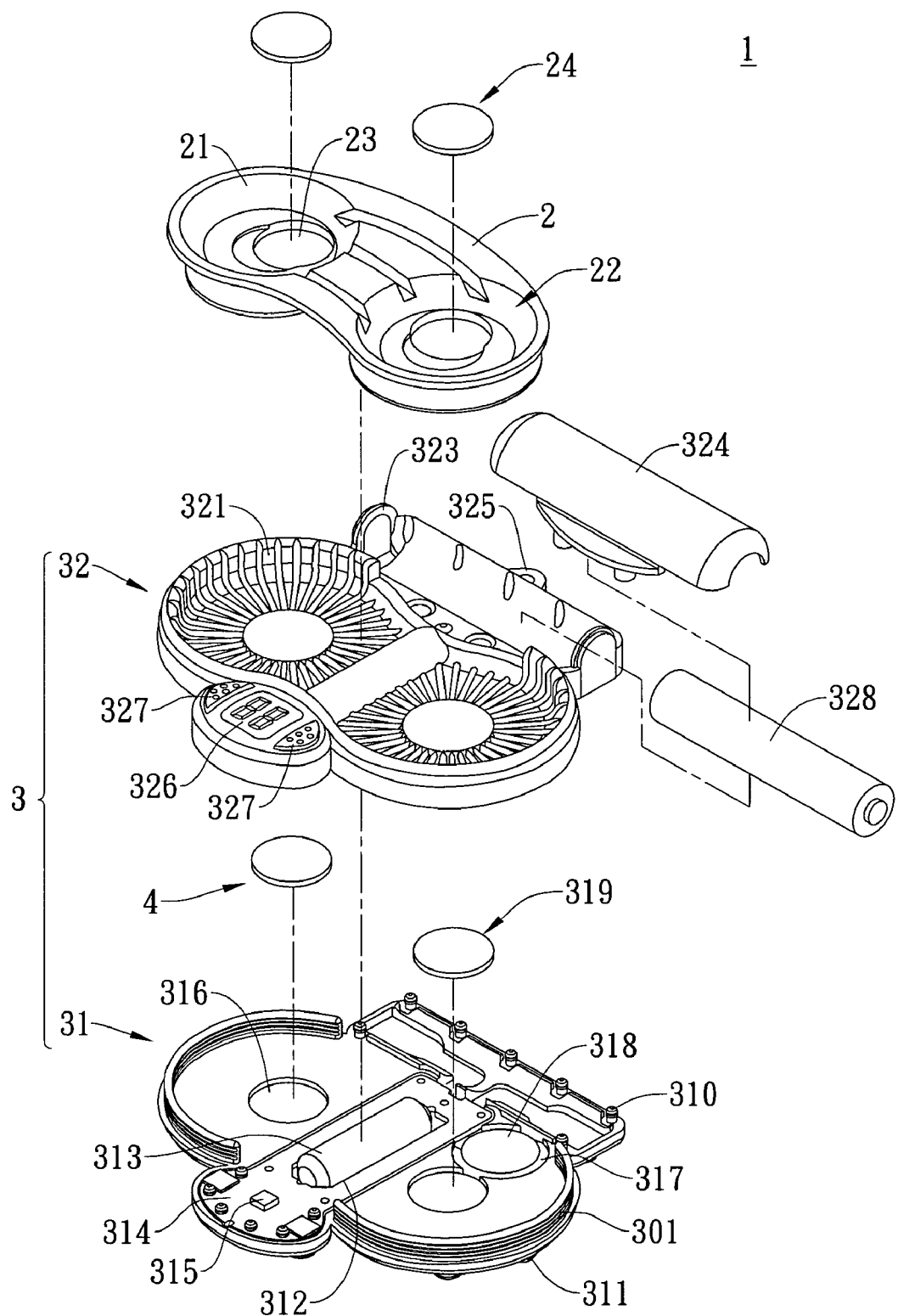
FIG. 2 is an exploded perspective view of the embodiment of the present invention.
Figure 3:
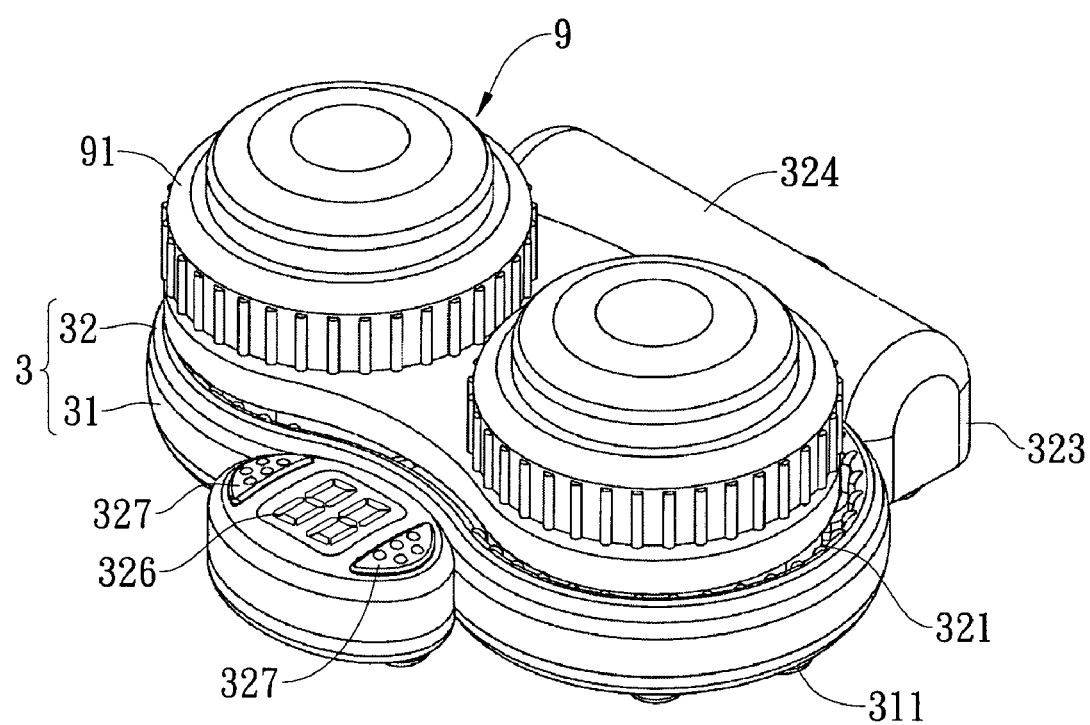
FIG. 3 is a perspective view of the embodiment of the present invention showing that a contact lens case is placed therein.

Please refer to FIGS. 1 and 2 that show a preferred embodiment of a vibration-type cleaning device 1 for contact lenses of the present invention. The vibration-type cleaning device 1 comprises an adaptor 2 and a base 3 and the adaptor 2 can support a contact lens case 9 thereon (as shown in FIG. 3).

The adaptor 2 is appropriately in flat shape. The left and right sides of the top of the adaptor 2 are provided respectively with a conical recess 21 and the two recesses form a support part 22. Each of the two recesses 21 has a bottom that is formed as a round recessed part 23 for placing and positioning a flat round magnet. The two magnets are used as a second magnetic piece 24. The left and right sides of the contact lens case 9 are provided respectively with a container 91. The two containers 91 are placed correspondingly into the two recesses 21 of the adaptor 2 and each container 91 is for containing clean solution and a contact lens. Besides, the bottom of the two containers 91 of the contact lens case 9 is permanently adhered to the adaptor 2. In practice, the two recesses 21 of the support part 22 can be formed into a single long recess for supporting the two containers 91 of the contact lens case 9.

Figure 4:
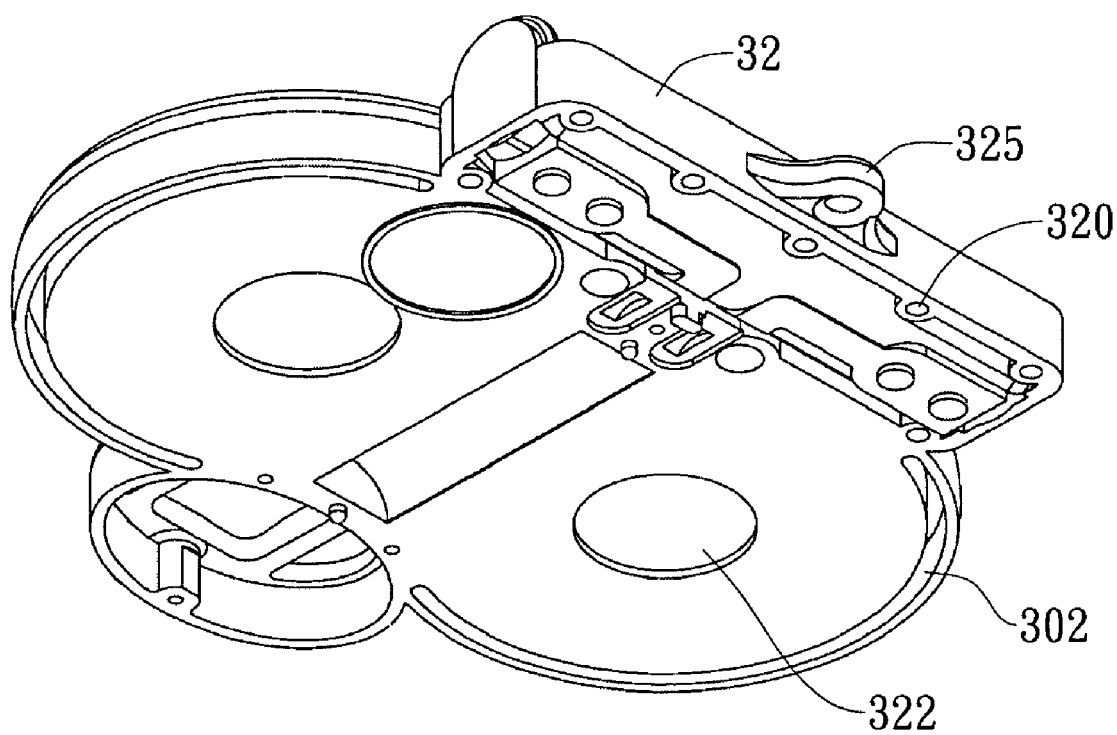
FIG. 4 shows a perspective view of a cover in the embodiment of the present invention.

The base 3 includes a bottom plate 31 and a cover 32. The cover 32 covers the bottom plate 31. The top of the cover 32 is provided with a recess 321 for placing the adaptor 2. The left and the right sides of the bottom of the cover 32 are provided respectively with a round upward recess 322 (as shown in FIG. 4). When the adaptor 2 is placed on the recess 321 of the cover 32, the two upward recesses 322 are directly under the two recessed parts 23 of the support part 22. The cover 32 is provided with a battery holder 323 at one side. The battery holder 323 has a cover 324 thereon and at least a battery 328 is placed therein as a direct current power source.

The battery holder 323 is provided with a fastening ring at one side and the fastening ring is used as a fastening part 325. The fastening part 325 can be connected with one end of a rope for fastening the cleaning device 1 to a fixed object, such as a table surface or a wall. Besides, another end of the rope also can be connected with a suction cup for attaching the cleaning device 1 to a table surface. Moreover, another side of the cover 32 is provided with a display 326. The left and the right sides of the display 326 are disposed respectively with a control button 327.

The bottom plate 31 is correspondingly attached to the bottom of the cover 32 via adhesives and the insertion of protrusions 310 provided on the bottom plate 31 into corresponding holes 320 of the cover 32. Two lateral rims 301 of the bottom plate 31 are engaged into two lateral grooves 302 of the cover 32. Besides, adhesives can be coated on the inner surfaces of the two lateral rims 301 for adhering the two lateral rims 301 into the two lateral grooves 302 of the cover 32. The protrusions 310 are provided at one side on the top of the bottom plate 31 while the corresponding holes 320 are provided on the bottom of the cover 32. The bottom plate 31 is provided with several elastic support legs 311 at its bottom. Besides, the bottom plate 31 can be made of elastic silica gel, polyurethane (PU), or other plastics with similar properties without being disposed with the elastic support legs 311. The top of the bottom plate 31 is provided with a long groove 312 for placing and positioning a round-rod vibrator 313. The vibrator 313 is in electric connection with the display 326, control buttons 327, the battery 328, and a microprocessor 315 on a circuit board 314. The left and right sides of the top of the bottom plate 31 are provided respectively with a round downward recess 316. The downward recess 316 is provided with another recess 317 at one side for locating a buzzer 318. The two downward recesses 316 are correspondingly provided under the two upward recesses 322 on the bottom of the cover 32 and form two spaces for locating and positioning respectively a flat round magnet. The two flat round magnets are used as a first magnetic piece 319. The first magnetic piece 319 and the second magnetic piece 24 form a positioning element 4.

In practice, at least a battery 328 can be used as a direct current power source for the vibrator 313. Besides, the vibrator 313 can also be provided with power by means of the combination of an alternative current power source and a rectifier. After soaking contact lenses into the containers 91 of the contact lens cases 9, users can control the operation of the microprocessor 315 and set the vibration time of the vibrator 313 by pressing the control buttons 327 to make the vibrator 313 vibrate the clean solution and the contact lenses in the contact lens case 9 and thus the cleaning effect of the contact lenses in the clean solution can be enhanced through vibration. Moreover, the time when users should dispose their contact lenses can be preset and consequently the users can be reminded of the time when they have to change their contact lenses. For example, the time when users have to dispose their contact lenses can, but not limited to, be shown on the display 326 in a countdown way.

Therefore, the present invention has the following advantages:

1. Adaptors of different specifications of the present invention can be attached to contact lens cases of corresponding specifications, so that the cost for buying different cleaning devices can be saved. Besides, the adaptor can be detached from the cleaning device and consequently it can be carried conveniently for users.
2. The base of the present invention is soundproof for reducing noise that is an undesirable side effect during the normal operation of vibrating the contact lenses in the contact lens case.
3. The fastening part of the present invention can be connected with a suction cup via a rope for attaching the cleaning device to a table surface, so that the movement of the cleaning device can be restricted to prevent the cleaning device from falling down to the ground while limited freedom of movement is still allowed to enhance vibration transmission.
4. The vibration time and the time when users have to dispose their contact lenses can be controlled by pressing the control button and can be shown by the display. Thereby, users can be reminded timely and the contact lenses can be cleaned effectively to extend the lifetime of the contact lenses.
5. The base and the adaptor of the present invention can be assembled together or detached from each other easily by means of two pairs of flat round magnets. Besides, by the use of the round-rod vibrator, the size of the cleaning device can be reduced when compared with the conventional cleaning devices for contact lenses.

Accordingly, as disclosed in the above description and attached drawings, the present invention can provide a cleaning device for contact lenses that is suitable for different specifications of contact lens cases and for economic purpose, is convenient to carry, and has effective cleaning function. It is new and can be put into industrial use.

Although the embodiments of the present invention have been described in detail, many modifications and variations may be made by those skilled in the art from the teachings disclosed hereinabove. Therefore, it should be understood that any modification and variation equivalent to the spirit of the present invention be regarded to fall into the scope defined by the appended claims.

What is claimed is:

1. A vibration-type cleaning device for contact lenses, comprising:
    an adapter having a support part thereon for supporting a contact lens case, a plane being located on a top of the adaptor;
    a base connected with the adapter via a positioning element and disposed with a vibrator therein, the vibrator extends along a longitudinal axis which fails to intersect the plane on the top of the adapter and which longitudinal axis fails to intersect the adaptor, the vibrator is connected with a power source that is for driving the vibrator, so that the contact lens case is vibratable to enhance cleaning effect,
    the positioning element includes a first magnetic piece and a second magnetic piece that are attractable with each other and the first magnetic piece is located in the base while the second magnet piece is located on the support part; and
    the base includes a bottom plate and a cover; the cover covers the bottom plate and the bottom plate is provided with a groove for placing the vibrator.

2. The vibration-type cleaning device for contact lenses as claimed in claim 1, further including a display, a microprocessor, and at least a control button, wherein the display, the microprocessor, and the control button are in electric connection with the power source and the vibrator.

3. The vibration-type cleaning device for contact lenses as claimed in claim 1, wherein the power source is a direct current power source.

4. The vibration-type cleaning device for contact lenses as claimed in claim 3, wherein the direct current power source is at least a battery.

5. The vibration-type cleaning device for contact lenses as claimed in claim 3, further including a display, a microprocessor, and at least a control button, wherein the display, the microprocessor, and the control button are in electric connection with the power source and the vibrator.

6. The vibration-type cleaning device for contact lenses as claimed in claim 1, wherein the base is made of elastic plastics.

7. The vibration-type cleaning device for contact lenses as claimed in claim 6, wherein the power source is a direct current power source.

8. The vibration-type cleaning device for contact lenses as claimed in claim 7, wherein the direct current power source is at least a battery.

9. The vibration-type cleaning device for contact lenses as claimed in claim 1, wherein the support part is a recess.

10. The vibration-type cleaning device for contact lenses as claimed in claim 1, wherein the contact lens case has two containers for placing contact lenses and the support part has two recesses for correspondingly supporting the containers.

11. The vibration-type cleaning device for contact lenses as claimed in claim 10, wherein the support part is a recess.

12. The vibration-type cleaning device for contact lenses as claimed in claim 1, wherein the contact lens case has two containers for placing contact lenses and the support part has two recesses for correspondingly supporting the containers, the vibrator being located below and between the two containers of the contact lens case.

13. The vibration-type cleaning device for contact lenses as claimed in claim 1 further including a fastening part that is disposed at the base and is connected with a rope for connecting the cleaning device to a fixed object.

14. The vibration-type cleaning device for contact lenses as claimed in claim 1, wherein the vibrator is a cylindrical vibration motor.

15. A vibration-type cleaning device for contact lenses, comprising:
    an adapter having a support part thereon for supporting a contact lens case, the contact lens case having two containers for receiving contact lenses;
    a base connected with the adapter via a positioning element and disposed with a vibrator therein, the vibrator extends along a longitudinal axis which fails to intersect the adapter, the vibrator is connected with a power source that is for driving the vibrator, so that the contact lens case is vibratable to enhance cleaning effect, the vibrator being located below and between the two containers of the contact lens case.

16. The vibration-type cleaning device for contact lenses as claimed in claim 15, further including a fastening part that is disposed at the base and is connected with a rope for connecting the cleaning device to a fixed object.

17. The vibration-type cleaning device for contact lenses as claimed in claim 15, further including a display, a microprocessor, and at least a control button, wherein the display, the microprocessor, and the control button are in electric connection with the power source and the vibrator.

18. The vibration-type cleaning device for contact lenses as claimed in claim 15, wherein the power source is a direct current power source.

19. The vibration-type cleaning device for contact lenses as claimed in claim 18, wherein the direct current power source is at least a battery.

20. The vibration-type cleaning device for contact lenses as claimed in claim 15, wherein the base is made of elastic plastics.

21. The vibration-type cleaning device for contact lenses as claimed in claim 15, wherein the longitudinal axis in which the vibrator extends would separate and fail to intersect the two containers of the contact lens case.

22. The vibration-type cleaning device for contact lenses as claimed in claim 15, wherein a plane is located on a top of the adaptor and wherein the longitudinal axis of the vibrator fails to intersect the plane on the top of the adapter.

23. The vibration-type cleaning device for contact lenses as claimed in claim 15 wherein the vibrator is a cylindrical vibration motor.

* * * * *